(12) United States Patent
Inoue et al.

(10) Patent No.: US 8,263,369 B2
(45) Date of Patent: Sep. 11, 2012

(54) COMPOUND CERAMIDASTIN, METHOD FOR PRODUCING THE SAME, AND USE OF THE SAME

(75) Inventors: Hiroyuki Inoue, Numazu (JP); Manabu Kawada, Numazu (JP); Daishiro Ikeda, Tokyo (JP)

(73) Assignee: Microbial Chemistry Research Foundation, Tokyo (JP)

( * ) Notice: Subject to any disclaimer, the term of this patent is extended or adjusted under 35 U.S.C. 154(b) by 0 days.

(21) Appl. No.: 13/037,684

(22) Filed: Mar. 1, 2011

(65) Prior Publication Data

US 2011/0213164 A1    Sep. 1, 2011

Related U.S. Application Data

(63) Continuation of application No. PCT/JP2009/064459, filed on Aug. 18, 2009.

(30) Foreign Application Priority Data

Sep. 2, 2008 (JP) ................. 2008-224606

(51) Int. Cl.
    *C12P 17/18* (2006.01)
    *C12N 1/00* (2006.01)
    *C07D 493/04* (2006.01)
    *A61K 31/343* (2006.01)
(52) U.S. Cl. .............. 435/119; 435/256.3; 514/460; 549/239
(58) Field of Classification Search .......... 549/239; 435/119, 256.3; 514/468
    See application file for complete search history.

(56) References Cited

FOREIGN PATENT DOCUMENTS

| EP | 1707211 | 10/2006 |
|---|---|---|
| JP | 08-301862 | 11/1996 |
| JP | 2002-284777 | 10/2002 |
| WO | 2007/029082 | 3/2007 |

OTHER PUBLICATIONS

Büchi et al., "Structures of Rubratoxins A and B." Journal of the American Chemical Society. 1970, vol. 92, No. 22. pp. 6638-6641.
Inoue et al.. "Ceramidastin, a novel bacterial ceramidase inhibitor, produced by Penicillium sp. Mer-F17067." The Journal of Antibiotics. 2009, vol. 62, pp. 63-67.
Okino et al.. "Purification and Characterization of a Novel Ceramidase from Pseudomonas aeruginosa." The Journal of Biological Chemistry. 1998, vol. 273. No. 23, pp. 14368-14373.
Okino et al., "Molecular Cloning, Sequencing, and Expression of the Gene Encoding Alkaline Ceramidase from Pseudomonas aeruginosa," The Journal of Biological Chemistry. 1999, vol. 274, No. 51, pp. 36616-36622.

*Primary Examiner* — Bernard Dentz
(74) *Attorney, Agent, or Firm* — Hamre, Schumann, Mueller & Larson, P.C.

(57) ABSTRACT

A compound having a structure expressed by the following Structural Formula (1):

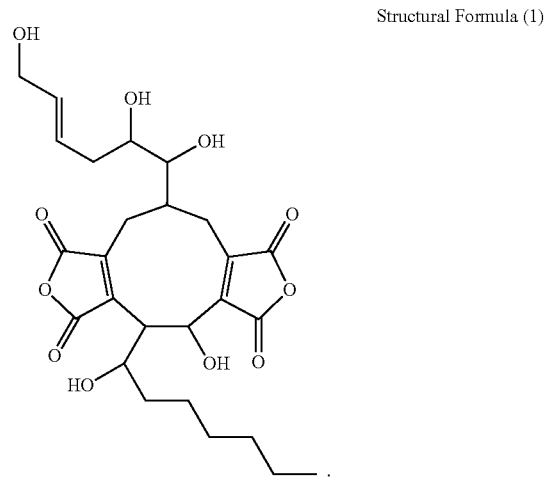

Structural Formula (1)

7 Claims, 6 Drawing Sheets

Ceramidastin (μg/mL)

Concentration (μg/mL)

COMPOUND CERAMIDASTIN, METHOD FOR PRODUCING THE SAME, AND USE OF THE SAME

CROSS-REFERENCE TO RELATED APPLICATION

This is a continuation application of PCT/JP2009/064459, filed on Aug. 18, 2009.

BACKGROUND OF THE INVENTION

1. Field of the Invention

The present invention relates to a novel compound having an inhibitory activity against at least one of neutral ceramidase and alkaline ceramidase, a method for producing the novel compound, use of the novel compound, and a novel microorganism that produces the novel compound.

2. Description of the Related Art

Atopic dermatitis is an intractable chronic eczema accompanied by intense itching and involving repeated aggravation and amelioration, and is thought to be caused in allergic constitution by various irritants derived from the environment.

The skin has a barrier function of preventing bacterial infection and water evaporation from bodies. This barrier function is degraded in atopic dermatitis. Then, bacterial infection, allergen invasion, etc. occur under extremely dry conditions, so that the symptom is further aggravated repeatedly. One known cause of the aggravation is neutral/alkaline ceramidase produced by *Pseudomonas aeruginosa* (see, for example, Okino et al. J. Biol. Chem. 273, 14368-14373, 1998; and Okino et al. J. Biol. Chem. 274, 36616-36622, 1999). That is, in one possible specific process through which atopic dermatitis is aggravated, ceramide of the skin of a patient with atopic dermatitis, who is infected with *Pseudomonas aeruginosa* in many cases, is decomposed and decreased by neutral/alkaline ceramidase produced by *Pseudomonas aeruginosa*, so that the barrier function of the skin is degraded.

Thus, a compound that inhibits ceramidase produced by *Pseudomonas aeruginosa* is expected to prevent a decrease of ceramide and hence prevent aggravation of atopic dermatitis. However, at present, there is no critically useful therapeutic method for atopic dermatitis, although the skin has been maintained clean and/or a steroid drug, a humectant, etc. have been applied for treating atopic dermatitis. Thus, demand has arisen for developments of a new compound having an excellent inhibitory activity against neutral/alkaline ceramidase and a more effective, safe novel therapeutic drug for atopic dermatitis.

BRIEF SUMMARY OF THE INVENTION

The present invention aims to solve the above existing problems to achieve the following objects. Specifically, an object of the present invention is to provide a novel compound having an inhibitory activity against at least one of neutral ceramidase and alkaline ceramidase, a method for producing the novel compound, a novel microorganism that produces the novel compound, and a ceramidase inhibitor or pharmaceutical composition containing the novel compound.

The present inventors conducted extensive studies to solve the above problems and have found that they could successfully isolate a strain belonging to the genus *Penicillium* as a novel microorganism producing a ceramidase inhibitor having a novel chemical structure. The present inventors analyzed the chemical structure of the ceramidase inhibitor to confirm that this ceramidase inhibitor was a novel compound. The present invention has been accomplished on the basis of the finding. Notably, the present inventors name the novel compound "ceramidastin."

The present invention is based on the above finding obtained by the present inventors. Means for solving the above existing problems are as follows.

<1> A compound having a structure expressed by the following Structural Formula (1):

Structural Formula (1)

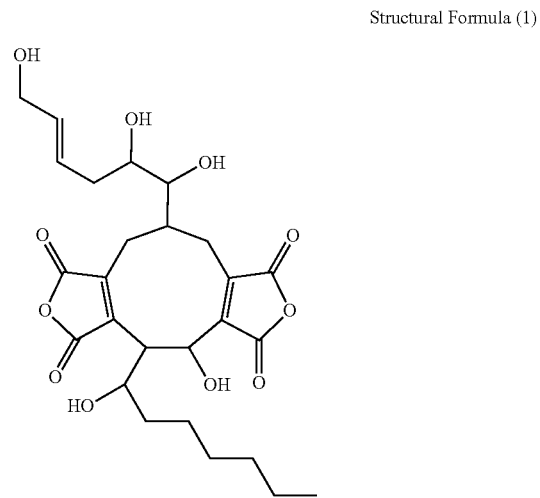

<2> A method for producing the compound according to <1>, including:

culturing a microorganism belonging to the genus *Penicillium* and capable of producing the compound according to <1>, and recovering the compound according to <1> from a culture obtained from the culturing.

<3> The method according to <2>, wherein the microorganism is a microorganism of *Penicillium* sp. Mer-f17067 strain deposited under accession number NITE P-580.

<4> A microorganism, wherein the microorganism belongs to the genus *Penicillium* and is capable of producing the compound according to <1>.

<5> The microorganism according to <4>, wherein the microorganism is a microorganism of *Penicillium* sp. Mer-f17067 strain deposited under accession number NITE P-580.

<6> A ceramidase inhibitor including:

the compound according to <1>, wherein the ceramidase inhibitor inhibits at least one of neutral ceramidase and alkaline ceramidase.

<7> A pharmaceutical composition including:

the compound according to <1>.

<8> The pharmaceutical composition according to <7>, wherein the pharmaceutical composition is a therapeutic drug for atopic dermatitis.

The present invention can provide a novel compound having excellent inhibitory activity against at least one of a neutral ceramidase and an alkaline ceramidase, a method for producing the novel compound, a novel microorganism that produces the novel compound, and a ceramidase inhibitor or pharmaceutical composition containing the novel compound. These can solve the existing problems to achieve the above objects.

DETAILED DESCRIPTION OF THE INVENTION (Compound)

A compound of the present invention has a structure expressed by the following Structural Formula (1). The compound having Structural Formula (1) is a novel compound separated by the present inventors (hereinafter may be referred to as "ceramidastin").

Structural Formula (1)

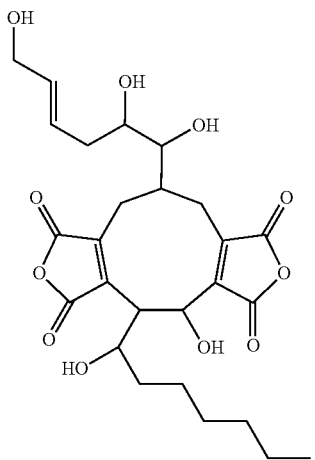

—Physico-Chemical Properties—

Physico-chemical properties of the compound having Structural Formula (1) are as follows.

(1) Color and appearance: white powder
(2) Molecular formula: $C_{26}H_{34}O_{11}$
(3) Mass spectrum (HRESI-MS) (m/z):
 (Negative mode): Found 521.20112 $(M-H)^-$
 : Calcd 521.20229 $(M-H)^-$
 (Positive mode): Found 545.20465 $(M+Na)^+$
 Calcd 545.19988 $(M+Na)^+$
(4) Melting point: 121° C. to 124° C.

Figure 1:
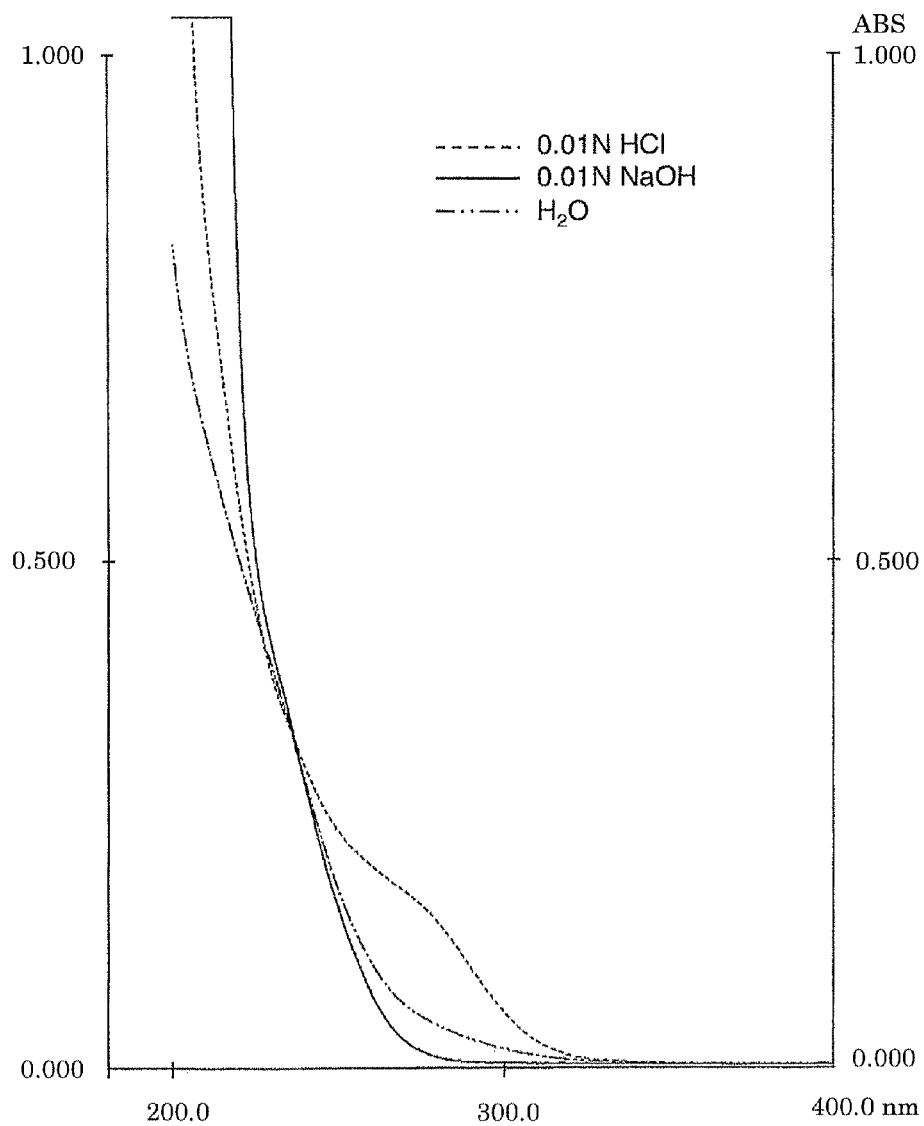
FIG. 1 is a UV absorption spectrum chart of ceramidastin in 0.01N HCl solution, 0.01N NaOH solution or water (vertical axis: absorbance (Abs), horizontal axis: wavelength (nm)).
Figure 2:
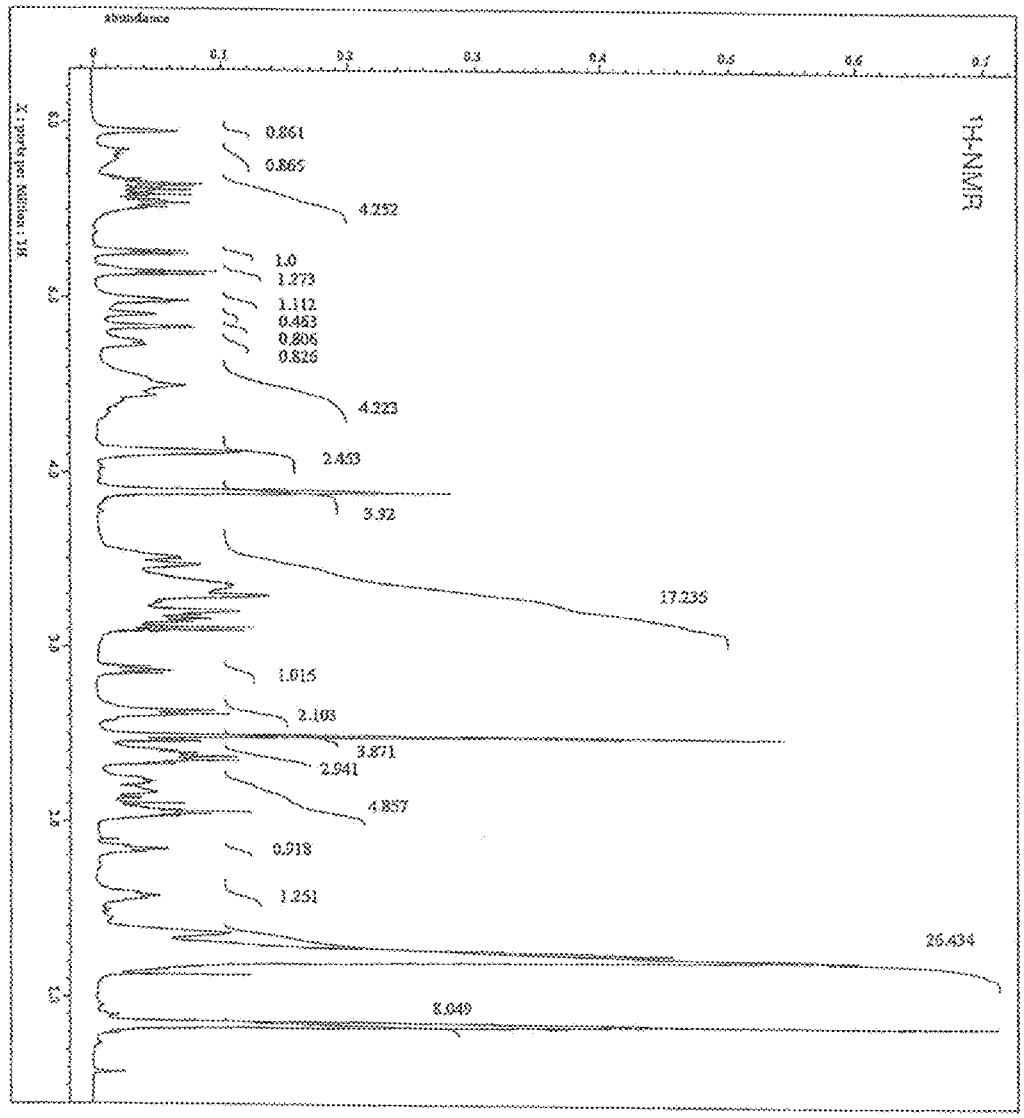
FIG. 2 is a $^1$H-NMR spectrum chart of ceramidastin measured in deuterated DMSO at 25° C. and 400 MHz (the unit of the horizontal axis: ppm).
Figure 3:
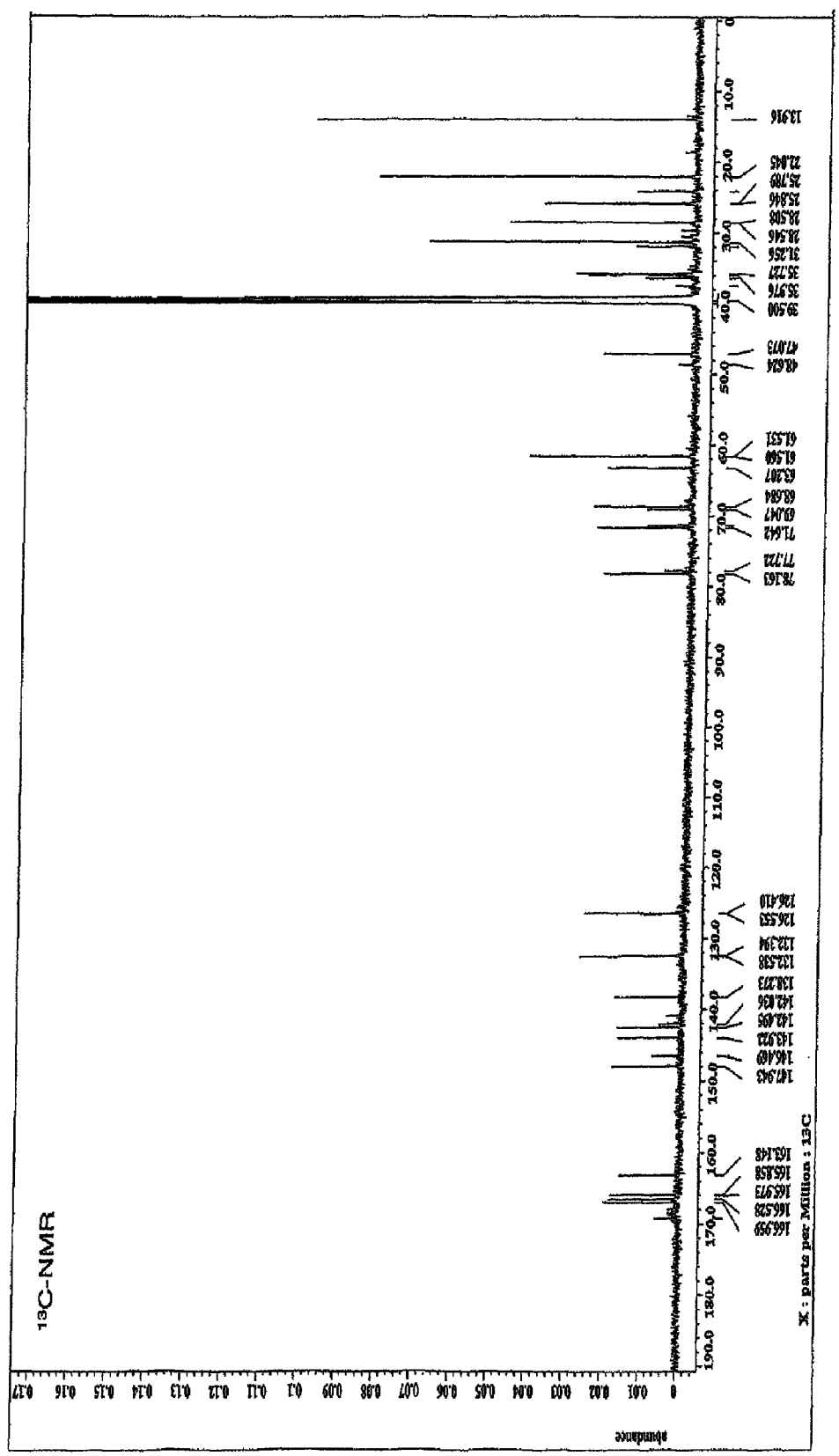
FIG. 3 is a $^{13}$C-NMR spectrum chart of ceramidastin measured in deuterated DMSO at 25° C. and 100 MHz (the unit of the horizontal axis: ppm).

(5) UV absorption spectrum:
 $\lambda_{max}$ nm
 [$H_2O$]: End
 [0.01N HCl]: 275 (sh)
 The UV absorption spectrum was measured with a Hitachi 228A spectrophotometer. FIG. 1 is a UV absorption spectrum chart.
(6) Specific optical rotation: $[\alpha]_D^{24}=+29.0°$ (c=0.57, $H_2O$)
(7) $^1$H-NMR spectrum (400 MHz, DMSO-$d_6$):
 δ(ppm): 0.85 (3H, t, J=7.0 Hz), 1.20, 1.20, 1.20, 1.23, 1.35, 1.85, 2.05, 2.25, 2.35, 2.45, 2.62, 2.80, 3.10 (1H, m), 3.20, 3.50 (1H, ddd, J=10.4, 7.2, 4.0 Hz), 3.90, 3.90 (2H, d, J=5.0 Hz), 4.12, 4.84, 4.90, 5.28 (1H, d, J=10.5 Hz), 5.55 (1H, dt, J=15.3, 5.0 Hz), 5.65 (1H, dt, J=15.3, 7.0 Hz), 5.95
 The $^1$H-NMR spectrum was measured with a JEOL JNM A400. FIG. 2 is a $^1$H-NMR spectrum chart.
(8) $^{13}$C-NMR spectrum (100 MHz, DMSO-$d_6$):
 δ(ppm): 13.5, 22.0, 24.1, 25.7, 28.0, 31.0, 31.8, 35.5, 35.8, 36.0, 47.0, 61.7, 63.0, 68.8, 71.5, 78.0, 126.5, 132.5, 138.4, 142.5, 143.8, 148.0, 163.0, 165.8, 166.4, 167.0
 The $^{13}$C-NMR spectrum was measured with a JEOL JNM A400. FIG. 3 is a $^{13}$C-NMR spectrum chart.

Whether a compound has a structure expressed by Structural Formula (1) can be determined with appropriately selected various analysis methods. This determination can be performed through, for example, mass spectrum analysis, UV absorption spectrum analysis, $^1$H-NMR spectrum analysis and $^{13}$C-NMR spectrum, as described above.

The ceramidastin may be obtained using ceramidastin-producing microorganisms or obtained through chemical synthesis. In particular, the ceramidastin is preferably obtained with the below-described method of the present invention.

The ceramidastin has excellent inhibitory activity against neutral/alkaline ceramidase as shown in the below-given Test Example 1. Thus, the ceramidastin can be suitably used as an active ingredient of, for example, the below-described ceramidase inhibitor or pharmaceutical composition of the present invention.

(Method for Producing the Compound)

A method for producing the compound of the present invention; i.e., ceramidastin includes at least a culturing step and a recovering step; and, if necessary, further includes other steps.

—Culturing Step—

The culturing step is a step of culturing a microorganism belonging to the genus *Penicillium* and capable of producing ceramidastin.

The microorganism is not particularly limited, so long as it belongs to the genus *Penicillium* and is capable of producing ceramidastin, and may be appropriately selected depending on the intended purpose. Examples thereof include a microorganism of *Penicillium* sp. Mer-f17067 strain isolated by the present inventors (NITE P-580, details will be described in the below "Microorganism" section). Also, other strains that are capable of producing ceramidastin can be routinely isolated from the natural world. Notably, through mutation treatments such as exposure to radiation, the microorganism of *Penicillium* sp. Mer-f17067 strain and other microorganisms capable of producing ceramidastin can be mutated so that they have increased production capability of ceramidastin. Moreover, through genetically engineering techniques, the microorganisms can be mutated so that they can produce ceramidastin.

The culturing at the culturing step is performed as follows. Specifically, microorganisms that produce ceramidastin (hereinafter may be referred to simply as "ceramidastin-producing microorganisms") are inoculated into a nutrient medium and cultured at a temperature suitable for the production of ceramidastin.

The nutrient medium is not particularly limited and may be appropriately selected depending on the intended purpose. Examples of the nutrient medium employable include known nutrient media that are conventionally used for culturing fungi.

The nutrient sources added to the nutrient medium are not particularly limited and may be appropriately selected depending on the intended purpose. The carbon source may be, for example, glucose, sucrose, glutinous starch syrup, dextrin, starch, glycerol, syrup, and animal and vegetable oils. The nitrogen source may be, for example, soy flour, wheat germ, corn steep liquor, cottonseed meal, meat extract, peptone, yeast extract, ammonium sulfate, sodium nitrate and urea. If necessary, inorganic salts releasing a sodium ion, a potassium ion, a calcium ion, a magnesium ion, a cobalt ion, a chlorine ion, a phosphate ion, a sulfate ion and other ions may be added. In addition, organic and inorganic compounds that facilitate the growth of the ceramidasitin-producing microorganisms and promote the production of ceramidasitin may be appropriately added. Any known materials for culturing fungi may be used so long as the ceramidasitin-producing microorganisms may utilize them to produce ceramidasitin.

The culturing method for the culturing is not particularly limited and may be appropriately selected depending on the intended purpose. Examples thereof include shake culturing, static culturing and tank culturing. In particular, aerobic culturing is preferred, with shake culturing being particularly preferred.

The temperature at the culturing is not particularly limited and may be appropriately determined depending on the intended purpose. The temperature is preferably 25° C. to 30° C., more preferably 25° C.

The culturing period is not particularly limited and may be appropriately determined in consideration of the amount of ceramidasitin accumulated. In general, the amount of ceramidastin accumulated becomes maximal for a culturing period of 2 days to 10 days.

—Recovering Step—

The recovering step is a step of recovering ceramidastin from a culture obtained from the culturing.

The ceramidastin has the above-described physico-chemical properties and thus, can be recovered from the culture utilizing these properties.

The recovering method is not particularly limited and may be appropriately selected depending on the intended purpose. In one employable method, ceramidastin is extracted from the culture using an organic solvent, and then the ceramidastin is purified for recovery with an adsorption-desorption method using an adsorbent, a molecule distribution method using a gel filtration agent, etc. In another employable method, the culture containing organic components is extracted with ethyl acetate; the resultant extract is concentrated under reduced pressure and then dissolved in a small amount of an organic solvent such as acetonitrile; and the resultant solution is treated through high-performance liquid chromatography using a solvent mixture such as acetonitrile/water, to thereby isolate and recover ceramidastin.

The method for producing the compound can be performed as described above to thereby obtain ceramidastin.

(Microorganism)

A microorganism of the present invention belongs to the genus *Penicillium* and can produce the above-described compound of the present invention; i.e., ceramidastin. The microorganism is not particularly limited and may be appropriately selected depending on the intended purpose, so long as it belongs to the genus *Penicillium*, can produce ceramidastin, and thus can be used as a ceramidastin-producing microorganism in the above-described method of the present invention.

In particular, *Penicillium* sp. Mer-f17067 strain is preferably used. The mycological characteristics of *Penicillium* sp. Mer-f17067 strain are as follows.

1. Properties in Various Media (1) Colonies formed on a potato dextrose agarose (PDA) plate, (2) a malt agar (MA) plate and (3) an automeal agar (OA) plate were observed visually and under an optical microscope. The results are shown as follows. Notably, the descriptions of colors are based on Methuen Handbook of colour (Kornerup and Wanscher, 1978).

(1) PDA Plate

Growth at 25° C.: this strain grew somewhat slower than the normal growth rate and in a range of 3.0 cm in diameter to 3.7 cm in diameter for one week after the beginning of culturing.

Color: Greyish blue (23C-4) to Orange (5A6-7)
Surface properties: fleecy to velvety
Production of soluble dyes: not observed (2) MA Plate Growth at 25° C.: this strain grew somewhat slower than the normal growth rate and in a range of 3.0 cm in diameter to 3.7 cm in diameter for one week after the beginning of culturing.

Color: Olive (1F-8) to Pale orange (5A-3)
Surface properties: velvety
Production of soluble dyes: not observed (3) OA Plate Growth at 25° C.: this strain grew somewhat slower than the normal growth rate and in a range of 3.0 cm in diameter to 3.7 cm in diameter for one week after the beginning of culturing.

Color: Dark green (25F-7) to Light orange (5A4-5)
Surface properties: fleecy to velvety
Production of soluble dyes: not observed 2. Morphological Characteristics Through observation under an optical microscope, hyphae were formed on the agar surface or inside the agar, and colorless, smooth septate hyphae were observed.

Conidia were formed so as to be adnate to vegetative hyphae, were colorless and had smooth surfaces. Biverticillate penicilli were mainly observed, in which metulae were formed from the tips of the conidia and phialides (i.e., conidium-forming cells) were formed at the tips of the metulae. The metulae each have a cylindrical shape and the phialides each have a needle shape. The conidia were phialoconidia, which were formed like chains from the phialides, had a subspherical to spherical shape, and were in the form of one cell and smooth in surface pattern.

The culture specimens obtained for about 2 weeks were found to form no sexually reproducible organs.

From the above-described mycological characteristics and molecular phylogenetic analysis based on the nucleotide sequence of the 28S rDNA-D1/D2 region, the Mer-f17067 strain is thought to belong to the genus *Penicillium*. Then, the Mer-f17067 strain is named *Penicillium* sp. Mer-f17067 strain.

Notably, the Mer-f17067 strain was requested for deposition to National Institute of Technology and Evaluation, Patent Microorganisms Depositary, and was accepted as NITE P-580.

Notably, as seen in other fungi, the Mer-f17067 strain easily changes in its properties. The microorganism of the present invention encompasses the Mer-f17067 strain-derived mutants (formed as a result of naturally-occurring mutations or inducible mutations), character zygotes, gene recombinants, etc. so long as they are capable of producing ceramidastin.

(Ceramidase Inhibitor and Pharmaceutical Composition)

—Ceramidase Inhibitor—

A ceramidase inhibitor of the present invention contains the above-described compound of the present invention; i.e., ceramidastin; and, if necessary, further contains other ingredients.

The ceramidase inhibitor of the present invention can be used as an inhibitor against at least one of a neutral ceramidase and an alkaline ceramidase.

The amount of the ceramidastin contained in the ceramidase inhibitor is not particularly limited and may be appropriately selected depending on the intended purpose. Also, the antimicrobial agent may be ceramidastin itself.

The other ingredients are not particularly limited and may be appropriately selected depending on the intended purpose from, for example, pharmacologically acceptable carriers. Examples of the other ingredients include ethanol, water and starch. The amount of the other ingredients contained in the ceramidase inhibitor is not particularly limited and may be appropriately selected depending on the intended purpose so that the effects of ceramidastin are not impaired.

Notably, the ceramidase inhibitor may be used alone or in combination with a drug containing other active ingredients. Also, the ceramidase inhibitor may be incorporated before use into the drug containing other active ingredients.

—Pharmaceutical Composition—

A pharmaceutical composition of the present invention contains the above-described compound of the present invention; i.e., ceramidastin; and, if necessary, further contains other ingredients.

The pharmaceutical composition of the present invention can inhibit neutral/alkaline ceramidase produced by *Pseudomonas aeruginosa*, and thus, can be particularly suitably used as a therapeutic drug for atopic dermatitis.

The amount of the ceramidastin contained in the pharmaceutical composition is not particularly limited and may be appropriately selected depending on the intended purpose. Also, the pharmaceutical composition may be ceramidastin itself.

The other ingredients are not particularly limited and may be appropriately selected depending on the intended purpose from, for example, pharmacologically acceptable carriers. Examples of the other ingredients include ethanol, water and starch. The amount of the other ingredients contained in the pharmaceutical composition is not particularly limited and may be appropriately selected depending on the intended purpose so that the effects of ceramidastin are not impaired.

Notably, the pharmaceutical composition may be used alone or in combination with a drug containing other active ingredients. Also, the pharmaceutical composition may be incorporated before use into the drug containing other active ingredients.

—Dosage Form—

The dosage form of the ceramidase inhibitor or the pharmaceutical composition is not particularly limited and may be appropriately selected depending on the intended purpose. Examples of the dosage form include powder, capsules, tablets, ointments and liquids. The ceramidase inhibitor or the pharmaceutical composition can be routinely formed into each of these dosage forms.

—Administration—

The administration method of the ceramidase inhibitor or the pharmaceutical composition is not particularly limited and may be appropriately selected depending on, for example, the dosage form of the ceramidase inhibitor or the pharmaceutical composition. The ceramidase inhibitor or the pharmaceutical composition can be administered orally or parenterally.

The dose of the ceramidase inhibitor or the pharmaceutical composition is not particularly limited and may be determined considering various factors of target individuals such as their age, body weight, constitution, symptoms and concomitant use of a drug containing other active ingredients.

The administration period of the ceramidase inhibitor or the pharmaceutical composition is not particularly limited and may be appropriately determined depending on the intended purpose. The animal species to which the ceramidase inhibitor or the pharmaceutical composition is administered is not particularly limited and may be appropriately selected depending on the intended purpose. Examples thereof include humans, monkeys, pigs, bovines, sheep, goats, dogs, cats, mice, rats and birds.

EXAMPLES

The present invention will next be described in detail by way of Examples and Test Examples, which should not be construed as limiting the present invention thereto. In Examples and Test Examples, the unit "%" means "% by mass" unless otherwise specified.

Example 1

Production of Ceramidastin

—Culturing Step—

A seed medium used was a liquid medium (whose pH had not been adjusted) containing potato starch 2.0%, glucose 1.0%, Soypro (product of J-Oil Mills Inc.) 2.0%, potassium dihydrogenphosphate 0.1%, magnesium sulfate heptahydrate 0.05% and three glass beads. The seed medium (100 mL) was dispensed into a 500 mL conical flask, followed by sterilizing at 120° C. for 15 min. One loopful of cells of *Penicillium* sp. Mer-f17067 strain (deposited as NITE P-580), which had been obtained through slant culturing on an agar, was inoculated on the above-treated medium. Then, the resultant medium was shake-cultured at 25° C. and 220 rpm for 3 days, to thereby obtain a seed culture liquid.

A production medium used was a liquid medium (pH 7) containing maltose hydrate 5.0%, Pharmamedia (product of Traders Protein) 1.5%, malt extract 1.0%, ammonium sulfate 0.5% and an aqueous mineral solution 1.0% by volume (containing as mineral ingredients cobalt(II) chloride hexahydrate 2.0%, calcium chloride 2.0% and magnesium chloride 2.0%). The production medium (100 mL) was dispensed into 500 mL-conical flask with baffle, followed by sterilizing at 120° C. for 15 min. Then, the above-obtained seed culture liquid (1 mL) was inoculated on the production medium, which was shake-cultured at 25° C. and 220 rpm for 4 days.

—Recovering Step—

The above-obtained culture liquid (5 L) was separated with a filter paper into the microorganisms and the culture supernatant. Subsequently, the culture supernatant was applied to a Diaion HP20 column (500 mL, product of Mitsubishi Chemical Corporation) for adsorption. Thereafter, the column was washed with 2 L of water and 2 L of 20% by volume acetone (acetone water=20:80, by volume), and then was eluted with 2 L of 75% by volume acetone (acetone water=75:25, by volume) to thereby obtain an eluate.

The acetone contained in the eluate was evaporated under reduced pressure. Subsequently, water was added to the obtained eluate so that the total amount was adjusted to 2.2 L. The pH of the resultant liquid was adjusted to 8 with 1% ammonium carbonate solution, and butanol of the same amount (2.2 L) was added thereto. The mixture was stirred and the aqueous layer was collected. The butanol contained in the thus-collected aqueous layer was evaporated under reduced pressure. Then, a 1 M potassium hydrogen sulfate aqueous solution was added portionwise to the thus-treated aqueous layer so that the pH was adjusted to 3. Thereafter, water was added to the resultant mixture so that the total amount was adjusted to 2.6 L. Then, the mixture was extracted twice with ethyl acetate of the half amount, and the ethyl acetate layer was collected. The thus-collected ethyl acetate layer was washed with saturated brine of the same amount, and dehydrated with sodium sulfate (anhydrate). Thereafter, the above-dehydrated ethyl acetate layer was concentrated and dried to thereby obtain 1.5 g of a crude product.

The crude product (1.5 g) was dissolved in 8.5 mL of 20% by volume acetonitrile-0.1% by volume TFA. The solution was subjected to HPLC (GL Sciences Inc., Inertsil ODS-3, inner diameter: 20 mm, length: 250 mm) five times using, as a developing solvent, 20% by volume to 60% by volume acetonitrile containing 0.1% by volume TFA (7 mL/min) and the ceramidastin-containing fractions were collected.

The above-collected fraction was diluted with 10 volumes of water, and then applied to Diaion HP20 column (500 mL, product of Mitsubishi Chemical Corporation) which had been equilibrated with water. After removal of TFA through washing with water, the column was eluted with 100% by volume acetone to thereby obtain an eluate.

The acetone contained in the eluate was evaporated under reduced pressure to thereby obtain a sample. Then, a 0.1% ammonium carbonate solution was added portionwise to the sample so that the pH thereof did not exceed 8, to thereby dissolve the sample. Thereafter, the dissolved sample was freeze-dried to obtain 245 mg of ceramidastin.

Through analysis, the obtained ceramidastin was found to have the physico-chemical properties as shown below. From the physico-chemical properties, it was confirmed that the ceramidastin was a novel compound having a structure expressed by the following Structural Formula (1).

(1) Color and appearance: white powder
(2) Molecular formula: $C_{26}H_{34}O_{11}$
(3) Mass spectrum (HRESI-MS) (m/z):
  (Negative mode): Found 521.20112 $(M-H)^-$
  : Calcd 521.20229 $(M-H)^-$
  (Positive mode): Found 545.20465 $(M+Na)^+$
  : Calcd 545.19988 $(M+Na)^+$
(4) Melting point: 121° C. to 124° C.
(5) UV absorption spectrum:
  $\lambda_{max}$ nm
  [$H_2O$]: End
  [0.01N HCl]: 275 (sh)
The UV absorption spectrum was measured with a Hitachi 228A spectrophotometer. FIG. 1 is a UV absorption spectrum chart.
(6) Specific optical rotation: $[a]_D^{24} = +29.0°$ (c=0.57, $H_2O$)
(7) $^1$H-NMR spectrum (400 MHz, DMSO-$d_6$):
  δ(ppm): 0.85 (3H, t, J=7.0 Hz), 1.20, 1.20, 1.20, 1.23, 1.35, 1.85, 2.05, 2.25, 2.35, 2.45, 2.62, 2.80, 3.10 (1H, m), 3.20, 3.50 (1H, ddd, J=10.4, 7.2, 4.0 Hz), 3.90, 3.90 (2H, d, J=5.0 Hz), 4.12, 4.84, 4.90, 5.28 (1H, d, J=10.5 Hz), 5.55 (1H, dt, J=15.3, 5.0 Hz), 5.65 (1H, dt, J=15.3, 7.0 Hz), 5.95
The $^1$H-NMR spectrum was measured with a JEOL JNM A400. FIG. 2 is a $^1$H-NMR spectrum chart.

(8) $^{13}$C-NMR spectrum (100 MHz, DMSO-$d_6$):
  δ(ppm): 13.5, 22.0, 24.1, 25.7, 28.0, 31.0, 31.8, 35.5, 35.8, 36.0, 47.0, 61.7, 63.0, 68.8, 71.5, 78.0, 126.5, 132.5, 138.4, 142.5, 143.8, 148.0, 163.0, 165.8, 166.4, 167.0
The $^{13}$C-NMR spectrum was measured with a JEOL JNM A400. FIG. 3 is a $^{13}$C-NMR spectrum chart.

Structural Formula (1)

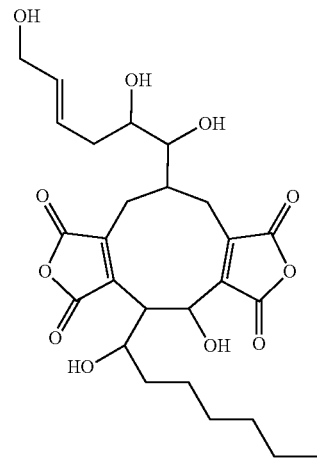

The obtained ceramidastin was measured for inhibitory activity against neutral/alkaline ceramidase in the following Test Example 1.

Test Example 1

—Production of Neutral/Alkaline Ceramidase—

A seed medium used was prepared as follows. Specifically, 3 g of Nissui Trypto-Soya Broth (product of Nissui Seiyaku) was dissolved in 100 mL of deionized water, and the resultant solution was dispensed into test tubes so that each test tube contained 3 mL of the solution, followed by high-pressure sterilization. Then, Pseudomonas aeruginosa (human clinical isolate) was inoculated into the seed medium in an amount of 2% by volume, and seed culturing was performed in a water bath at 37° C. and 100 rpm for 3 hours.

A synthetic medium for main culturing was prepared as follows. Specifically, ammonium chloride (0.05%), dipotassium hydrogenphosphate (0.05%) and sodium chloride (0.5%) were dissolved in deionized water; the pH of the resultant solution was adjusted to 7.2, followed by high-pressure sterilization; and the thus-sterilized medium was supplemented with Taurodeoxycholate (product of Sigma-Aldrich Co.) and Sphingomyelin (product of Sigma-Aldrich Co.), which had been dissolved in methanol, so that the concentration of each compound was adjusted to 0.05% (Okino et al J. Biol. Chem. 273, 14368-14373, 1998). The synthetic medium for main culturing was dispensed into sterilized test tubes so that each test tube contained 3 mL of the medium. Then, the above-obtained seed culture liquid of Pseudomonas aeruginosa was inoculated into the synthetic medium in an amount of 2% by volume, and main culturing was performed in a water bath at 30° C. and 100 rpm for 24 hours. Twenty-four hours after, the culture liquid was sterilized through filtration with KURABO Steradisc 25 (0.2 μm) (product of KURABO INDUSTRIES LTD.) to thereby obtain an enzyme liquid of neutral/alkaline ceramidase.

—Neutral/Alkaline Ceramidase Activity Inhibitory Test—

The above-obtained enzyme liquid of neutral/alkaline ceramidase was used to perform neutral/alkaline ceramidase activity inhibitory test as follows.

Neutral/alkaline ceramidase activity was measured according to the method used by Okino et al. (J. Biol. Chem. 273, 14368-14373, 1998) with minor modifications.

First, a ceramidastin solution (5 μL) was added to the wells of a propylene 96-well plate. The ceramidastin solution used was a solution in which the final concentration of ceramidastin was 0 μg/mL (control), 200 μg/mL, 100 μg/mL, 50 μg/mL, 25 μg/mL, 12.5 μg/mL, 6.25 μg/mL, 3.12 μg/mL or 1.56 μg/mL.

Also, a substrate liquid was prepared as follows. Specifically, 500 μL of 50 mM Tris-HCl buffer (pH 8.5) was added to a glass tube on ice. Separately, C12-NBD Ceramide (7-nitrobenz-2-oxa-1,3-diazole (NBD)-labeled N-dodecanoyl-sphinogosine, product of Avanti Polar Lipids) was dissolved in chloroform-methanol (2:1, by volume) at a concentration of 1.8 mM. Then, 3 μL of the resultant ceramide solution was added to the glass tube, followed by stirring for dissolution.

The substrate liquid (10 μL) and the enzyme liquid of neutral/alkaline ceramidase (10 μL) were added to each well of the 96-well plate containing the ceramidastin solution, and were allowed to react at 37° C. for 2.5 hours.

Then, 100 μL of chloroform-methanol (2:1, by volume) was added to each well to terminate the reaction. After drying with a vacuum pump, 100 μL, of chloroform-methanol (2:1, by volume) was added to the resultant product, whereby a solution was obtained.

The above solution (20 μL) was spotted onto a TLC plate (MERCK 25 TLC plates 20 cm×20 cm Silica gel 60 $F_{254}$) and developed (chloroform:methanol ammonia (25%)=90:20:0.5, by volume). Subsequently, Image Reader FLA 5000 (product of FUJIFILM Corporation) was used to measure the fluorescence derived from the substrate, and Science Lab 2001 ImageGauge (product of FUJIFILM Corporation) was used to calculate the inhibitory rate of substrate decomposition.

Figure 4:
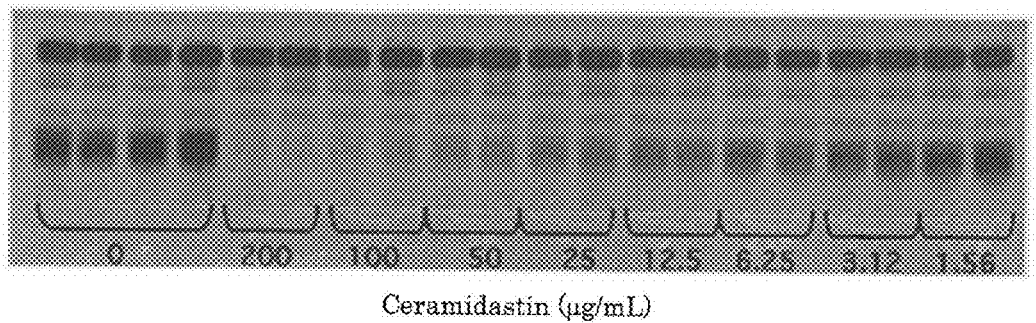
FIG. 4 is an image of TLC performed in Test Example 1.
Figure 5:
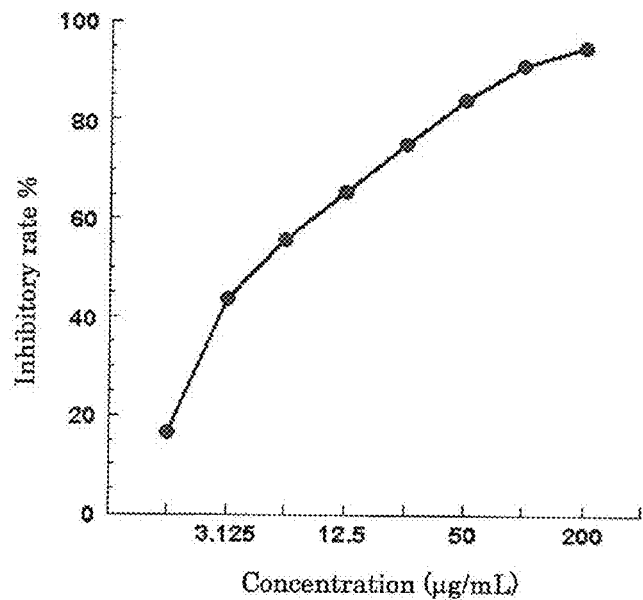
FIG. 5 is a graph indicating the inhibitory activity of ceramidase against neutral/alkaline ceramidase.

FIG. 4 shows the results of TLC. FIG. 5 is a graph of neutral/alkaline ceramidase inhibitory activity of ceramidastin.

The above-obtained results indicate that the neutral/alkaline ceramidase inhibitory activity of ceramidastin was 6.25 μg/mL in terms of $IC_{50}$ (the concentration required for 50% inhibition of enzyme activity), and thus ceramidastin had excellent inhibitory activity.

Test Example 2

—Therapeutic Effects on Atopic Dermatitis-Like Model Mice—

Atopic dermatitis-like model mice were used to test ceramidastin for the therapeutic effects on atopic dermatitis. Specifically, the above-obtained enzyme liquid was applied onto the mice to examine the aggravation degree of corneal layer of epidermis and inflammation. In addition, the enzyme liquid and ceramidastin were applied thereonto to examine the effects on the skin brought by inhibiting neutral/alkaline ceramidase activity.

The atopic dermatitis-like model mice used were 6-week-old NC/Nga female mice (product of Charles River). The above NC/Nga mice are used as an atopic dermatitis model (Hiroi et al. Jpn. J. Pharmacol. 76, 175-183, 1998) and have an increased number of mast cells in the skin tissue.

—Defatting—

Hair was removed in advance from the 6-week-old NC/Nga female mice under anesthesia (six mice for each group). Subsequently, absorbent cotton impregnated with acetone-ether (1:1) was pressed for 15 sec against them under anesthesia by nembutal. Then, absorbent cotton impregnated with sterilized distilled water pressed for 30 sec against them, to thereby remove sebum cutaneum (defatting).

—Application of Neutral/Alkaline Ceramidase—

After defatting, 0.2 mL of the enzyme liquid, which had been 4-fold diluted, was applied onto the skin.

—Application of Ceramidastin—

Thirty minutes after the application of neutral/alkaline ceramidase, 0.2 mL of a ceramidastin solution in sterilized distilled water (1 mg/mL) was applied.

The procedure of the above defatting and applications of ceramidase and ceramidastin was repeated 47 times in total so that it was performed twice in the morning and evening for 5 days a week. Then, the skin was excised, fixed in formaline solution and embedded in paraffin, to thereby form tissue pieces. The thus-formed tissue pieces were stained with toluidine blue, and the number of mast cells in the tissue was counted under a microscope.

Figure 6:
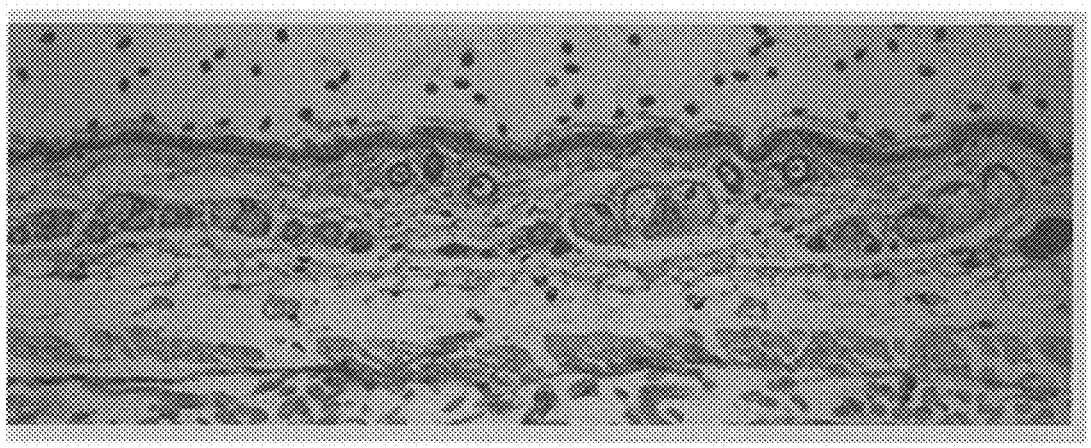
FIG. 6 is an image of the toluidine blue-stained skin piece of the mouse having undergone only defatting.
Figure 7:
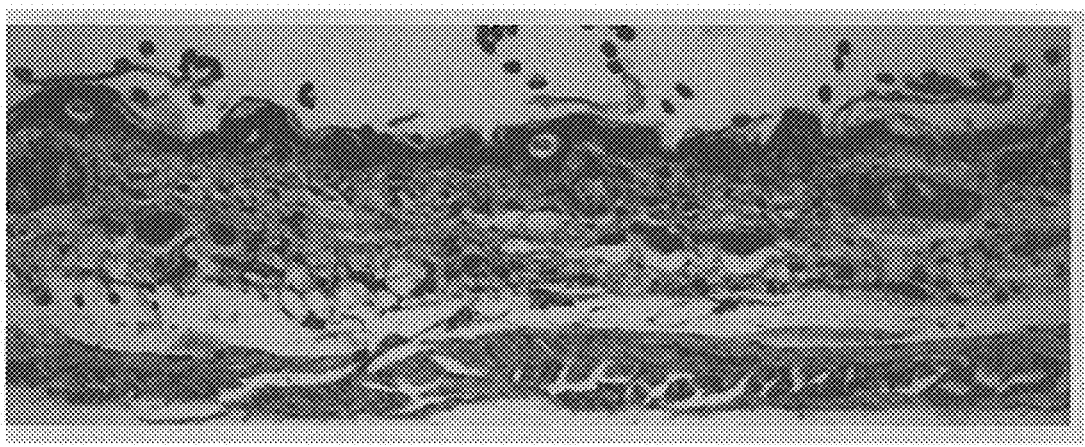
FIG. 7 is an image of the toluidine blue-stained skin piece of the mouse having undergone defatting and application of neutral/alkaline ceramidase.
Figure 8:
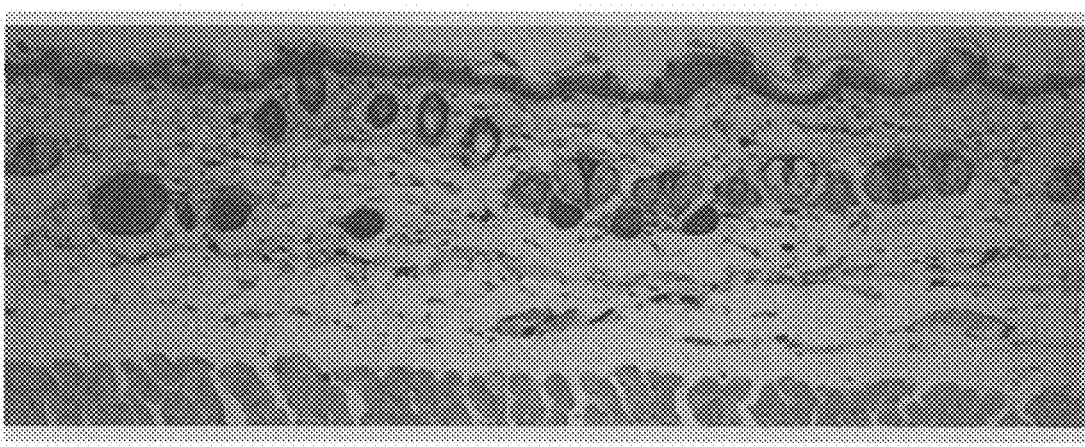
FIG. 8 is an image of the toluidine blue-stained skin piece of the mouse having undergone defatting and applications of neutral/alkaline ceramidase and ceramidastin.

FIG. 6 is an image of the toluidine blue-stained skin piece of the mouse which had undergone only defatting (hereinafter may be referred to as an "untreated skin piece"). FIG. 7 is an image of the toluidine blue-stained skin piece of the mouse which had undergone defatting and application of neutral/alkaline ceramidase (hereinafter may be referred to as a "ceramidase-applied skin piece"). FIG. 8 is an image of the toluidine blue-stained skin piece of the mouse which had undergone defatting and the applications of neutral/alkaline ceramidase and ceramidastin (hereinafter may be referred to as a "ceramidase+ceramidastin-applied skin piece").

Figure 9:
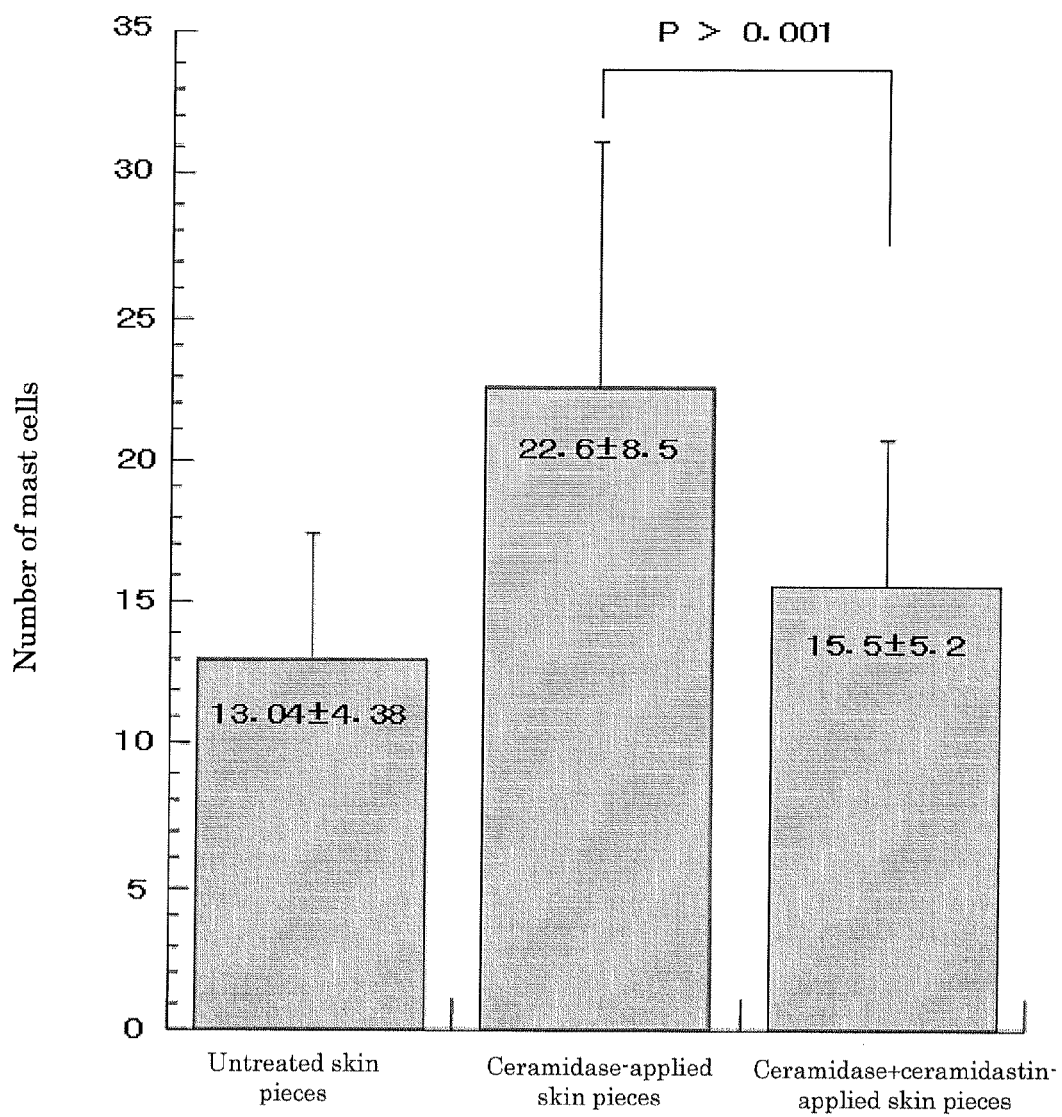
FIG. 9 is a graph of the number of mast cells in mouse skin pieces.

FIG. 9 is a graph of the number of mast cells in the mouse skin pieces. The number of mast cells was found to be 13.04±4.38 in the "untreated skin pieces," to be 22.6±8.5 in the "ceramidase-applied skin pieces," and to be 15.5±5.2 in the "ceramidase+ceramidastin-applied skin pieces." Also, significant difference (P>0.001) was observed between the "ceramidase-applied skin pieces" and the "ceramidase+ceramidastin-applied skin pieces."

From the above-obtained results, the number of mast cells was found to increase in the "ceramidase-applied skin pieces" as compared with the "untreated skin pieces," and also, corneal layer of epidermis and inflammation were found to be aggravated. In the "ceramidase+ceramidastin-applied skin pieces," an increase in the number of mast cells was significantly inhibited.

A novel compound (ceramidastin) of the present invention has an excellent inhibitory activity against neutral/alkaline ceramidase, and thus can be suitably used as a new ceramidase inhibitor. Also, this novel compound is useful for a pharmaceutical composition for, among others, prevention and treatment of skin diseases caused by bacterial infection such as atopic dermatitis.

What is claimed is:

1. A compound having a structure expressed by following Structural Formula (1):

Structural Formula (1)

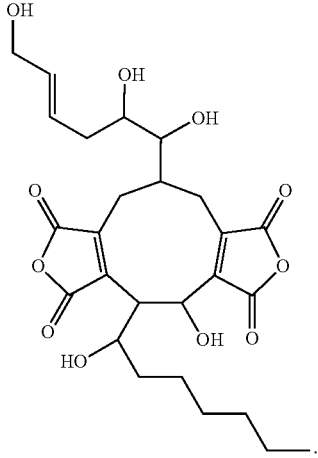

2. A method for producing a compound having a structure expressed by following Structural Formula (1), comprising:

culturing a microorganism belonging to genus *Penicillium* and capable of producing the compound and obtaining a culture of the microorganism; and recovering the compound from the culture obtained from the culturing step, wherein the microorganism is an isolated microorganism of *Penicillium* sp. Mer-f17067 strain deposited under accession number NITE P-580

Structural Formula (1)

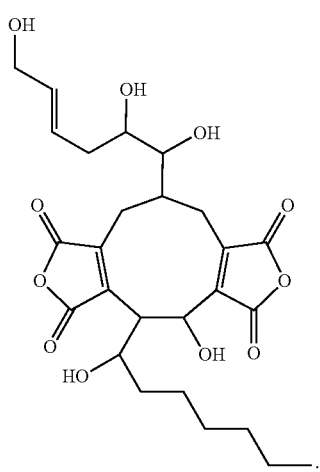

3. A microorganism,
wherein the microorganism belongs to genus *Penicillium* and is capable of producing a compound having a structure expressed by following Structural Formula (I),
wherein the microorganism is an isolated microorganism of *Penicillium* sp. Mer-f17067 strain deposited under accession number NITE P-580

Structural Formula (1)

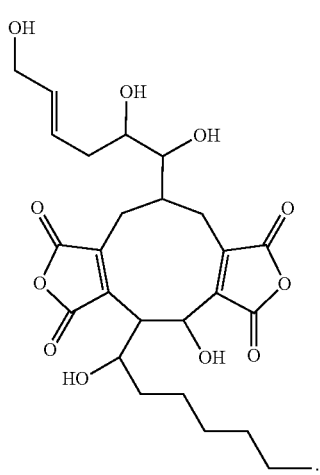

4. A ceramidase inhibitor comprising:
a compound having a structure expressed by following Structural Formula (1), wherein the ceramidase inhibitor inhibits at least one enzyme selected from the group consisting of neutral ceramidase and alkaline ceramidase, Structural Formula (1)

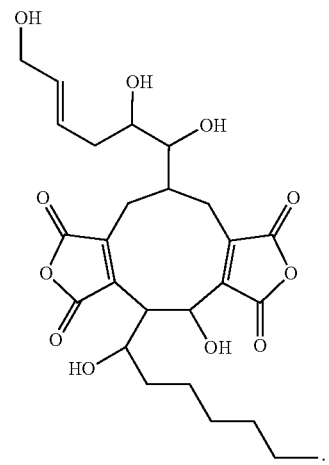

5. A pharmaceutical composition comprising:
a compound having a structure expressed by following Structural Formula (1):

Structural Formula (1)

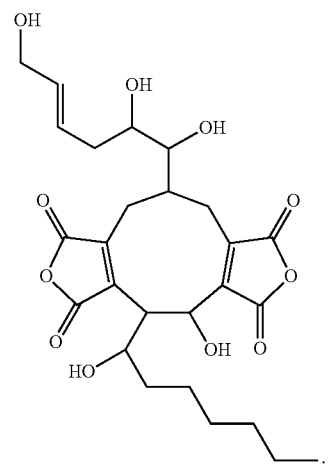

6. The pharmaceutical composition according to claim 5, wherein the pharmaceutical composition comprises an effective amount of the compound for treating atopic dermatitis.

7. A method of treating atopic dermatitis comprising: administering the pharmaceutical composition according to claim 6 to a subject who has atopic dermatitis.

* * * * *